United States Patent
Coulomb

(10) Patent No.: US 11,091,722 B2
(45) Date of Patent: Aug. 17, 2021

(54) COMPOUND HAVING A MUGUET ODOR

(71) Applicant: Firmenich SA, Satigny (CH)

(72) Inventor: Julien Coulomb, Geneva (CH)

(73) Assignee: Firmenich SA, Satigny (CH)

(*) Notice: Subject to any disclaimer, the term of this patent is extended or adjusted under 35 U.S.C. 154(b) by 68 days.

(21) Appl. No.: 15/744,100

(22) PCT Filed: Jul. 7, 2016

(86) PCT No.: PCT/EP2016/066142
§ 371 (c)(1),
(2) Date: Jan. 12, 2018

(87) PCT Pub. No.: WO2017/009175
PCT Pub. Date: Jan. 19, 2017

(65) Prior Publication Data
US 2018/0201873 A1    Jul. 19, 2018

(30) Foreign Application Priority Data
Jul. 14, 2015 (EP) .................................... 15176627

(51) Int. Cl.
*C11B 9/00* (2006.01)
*C11D 3/50* (2006.01)
*C07C 47/27* (2006.01)
*A61Q 13/00* (2006.01)
*A61K 8/34* (2006.01)
*A61Q 19/00* (2006.01)
*C07C 47/225* (2006.01)

(52) U.S. Cl.
CPC .............. *C11B 9/0061* (2013.01); *A61K 8/34* (2013.01); *A61Q 13/00* (2013.01); *A61Q 19/00* (2013.01); *C07C 47/225* (2013.01); *C07C 47/27* (2013.01); *C11D 3/50* (2013.01); *A61K 2800/10* (2013.01)

(58) Field of Classification Search
CPC .................................................... C11B 9/0061
See application file for complete search history.

(56) References Cited

U.S. PATENT DOCUMENTS 4,396,670 A    8/1983  Sinclair
4,491,537 A    1/1985  Fujioka et al.

FOREIGN PATENT DOCUMENTS

WO    WO2001041915 A1    6/2001
WO    WO2014180945 A1    11/2014
WO    WO2014180952 A1    11/2014
WO    WO2014207205 A1    12/2014

OTHER PUBLICATIONS

International Search Report and Written Opinion, application PCT/EP2016/066142 dated Sep. 15, 2016.
Bone et al., "Microencapsulated Fragrances in Melamine Formaldehyde Resins, Chimia," 2011, vol. 65, n° 3, pp. 177-181.
Dietrich et al., "Amino resin microcapsules, I. Literature and patent review," Acta Polymerica, (1989) vol. 40, n° 4, pp. 243-251.
Dietrich et al., "Amino resin microcapsules, II. Preparation and morphology," Acta Polymerica, (1989) vol. 40, n° 5, pp. 325-331.
Dietrich et al., "Amino resin microcapsules, III Release properties," Acta Polymerica, (1989) vol. 40, n° 11, pp. 683-690.
Dietrich et al., Amino resin microcapsules, IV, Surface tension of the resins and mechanism of capsule formation, Acta Polymerica, (1990) vol. 41, n° 2, pp. 91-95.
Herrmann, "Controlled Release of Volatiles under Mild Reaction Conditions: From Nature to Everyday Products," Angew. Chem. Int. Ed., vol. 46, pp. 5836-5863 (2007).
Lee et al., "Microencapsulation of fragrant oil via in situ polymerization: effects of pH and melamine-formaldehyde molar ratio," J. Microencapsulation, 2002, vol. 19, 559-569.

*Primary Examiner* — Arrie L Reuther
(74) *Attorney, Agent, or Firm* — Armstrong Teasdale LLP

(57) ABSTRACT

The present invention relates to phenylpropanal derivatives of formula (I)

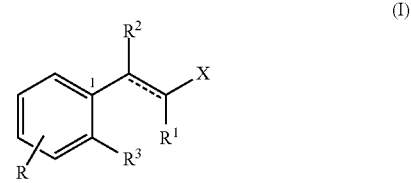

(I)

in the form of any one of its stereoisomers or a mixture thereof, and wherein the dotted line represents a carbon-carbon single or double bond; X represents a CN or CHO group; each $R^1$, $R^2$ and $R^3$ independently from each other, represents a hydrogen atom or a $C_{1-2}$ alkyl group; and R represents a group of formula $-[CH_2]_nC(Me)_2OH$, wherein n is 1 or 2; said R being a meta or para substituent of the aromatic ring, relative position 1;
and their uses as perfuming ingredients as well as the composition and consumer product including such derivatives.

14 Claims, No Drawings

COMPOUND HAVING A MUGUET ODOR

RELATED APPLICATIONS

This application is a national stage application under 35 U.S.C. § 371 filing of International Patent Application PCT/EP2016/066142, filed Jul. 7, 2016, which claims the benefit of European patent application n° 15176627.6 filed Jul. 14, 2015.

TECHNICAL FIELD

The present invention relates to the field of perfumery. More particularly, it concerns phenylpropanal derivatives of formula (I) as perfuming ingredients as well as the composition and consumer product including such derivatives.

BACKGROUND

To the best of our knowledge, the present compounds are novel.

To the best of our knowledge, only one closely related structural analogue has been reported in the literature as perfuming ingredient, namely 3-(4-(2-hydroxypropan-2-yl) phenyl)butanal reported in U.S. Pat. No. 4,491,537 as having a green, woody, peach like aroma, i.e. a totally different organoleptic profile from the present invention's compounds. Moreover, this document does not report or suggest any organoleptic properties of the compounds of formula (I), or any use of said compounds in the field of perfumery.

DESCRIPTION OF THE INVENTION

We have now surprisingly discovered that a compound of formula

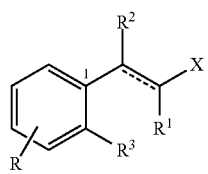

(I)

in the form of any one of its stereoisomers or a mixture thereof, and wherein the dotted line represents a carbon-carbon single or double bond;
X represents a CN or CHO group;
each $R^1$, $R^2$ and $R^3$ independently from each other, represents a hydrogen atom or a $C_{1-2}$ alkyl group; and
R represents a group of formula —[$CH_2$]$_n$C(Me)$_2$OH, wherein n is 1 or 2; said R being a meta or para substituent of the aromatic ring, relative position 1;
can be used as perfuming ingredient, for instance to impart odor notes of the lily of the valley type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the double bond is in a conformation E or Z.

According to any one of the above embodiments of the invention, said compound can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomers E represent at least 50% of the total mixture, or even at least 75% (i.e a mixture E/Z comprised between 75/25 and 100/0).

For the sake of clarity, by the expression "wherein the dotted line represents a carbon-carbon single or double bond", or the similar, it is meant the normal meaning understood by a person skilled in the art, i.e. that the whole bonding (solid and dotted line) between the carbon atoms connected by said dotted line is a carbon-carbon single or double bond.

According to any one of the embodiments of the invention, said compound (I) is a compound of formula

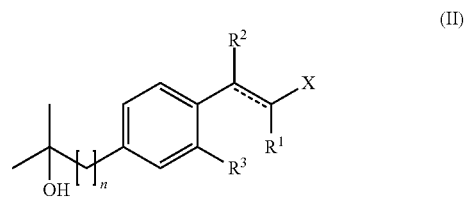

(II)

in the form of any one of its stereoisomers or a mixture thereof, and wherein the dotted line represents a carbon-carbon single or double bond;
n is 1 or 2;
X represents a CN or CHO group; and
and each $R^1$, $R^2$ and $R^3$ independently from each other, represents a hydrogen atom or a $C_{1-2}$ alkyl group.

According to any one of the embodiments of the invention, said invention's compound is a $C_{12}$-$C_{16}$, or even a $C_{13}$-$C_{14}$, compound.

According to any one of the embodiments of the invention, said invention's compound is a compound of formula

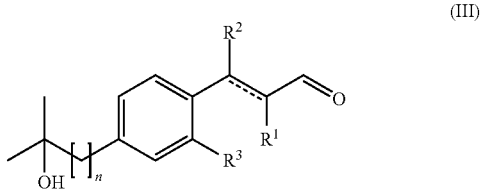

(III)

wherein the dotted line, n, $R^1$, $R^2$ and $R^3$ have the same meaning as indicated above.

According to any one of the embodiments of the invention, said invention's compound is a compound wherein the dotted line represents a carbon-carbon single bond.

According to any one of the embodiments of the invention, said invention's compound is a compound of formula

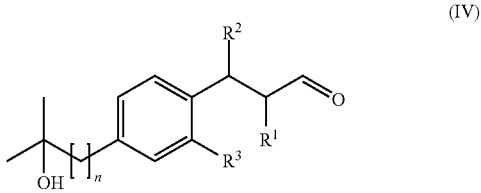

(IV)

wherein n, $R^1$, $R^2$ and $R^3$ have the same meaning as indicated above.

According to any one of the embodiments of the invention, said invention's compound, is a compound wherein n represents 1.

According to any one of the embodiments of the invention, said invention's compound is a compound wherein and each $R^1$, $R^2$ and $R^3$, independently from each other, represents a hydrogen atom or a methyl group. In particular one or two of said $R^1$, $R^2$ and $R^3$ may represent a hydrogen atom, and the other or others a hydrogen atom or a methyl group.

According to any one of the embodiments of the invention, said invention's compound is a compound wherein $R^2$ may represent a hydrogen atom, and one of $R^1$ and $R^3$ are each, independently from each other, a hydrogen atom or a methyl group. In particular $R^1$ may represent a hydrogen atom, and one of $R^2$ and $R^3$ is a hydrogen atom and the other is a hydrogen atom or a methyl group.

To the best of our knowledge, the compounds of formula (I) as herein above reported are novel, and therefore also an object of the present invention.

As specific examples of the invention's compounds, one may cite, as non-limiting example, 3-[4-(2-hydroxy-2-methylpropyl)phenyl]propanal, which is characterized by having a nice and well balanced floral, lily of the valley, hydroxycitronellal odor note, and an overall olfactive character reminding strongly of the one of the very well-known ingredient Lyral® (4/3-(4-hydroxy-4-methylpentyl)-3-cyclohexene-1-carbaldehyde; origin International Flavors & Fragrances, USA). This striking resemblance is of high interest for the industry since Lyral® is now limited in use for allergen reasons and the industry is still waiting for olfactive substitutes for this ingredient.

In fact, when 3-[4-(2-hydroxy-2-methylpropyl)phenyl] propanal is compared with Lyral®, the invention's compound distinguishes itself by being more substantive and powerful (thus allowing even lower level of dosage compared to the prior art compound) as well as having an improved radiance, while (to the contrary of many supposed substitute of Lyral®) delivering also the unique "wet" effect of Lyral®.

As other specific, but non-limiting, examples of the invention's compounds, one may cite the following ones in Table 1:

TABLE 1

Invention's compounds and their odor properties

| Compound structure and name | Odor notes |
|---|---|
| 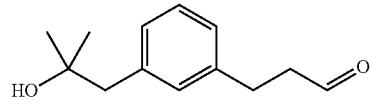<br>3-(3-(2-hydroxy-2-methylpropyl)phenyl)propanal | aldehydic, lyral |
| 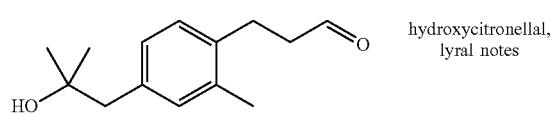<br>3-[4-(2-hydroxy-2-methylpropyl)-2-methylphenyl]propanal | hydroxycitronellal, lyral notes |

According to a particular embodiment of the invention, the compounds of formula (I) are 3-[4-(2-hydroxy-2-methylpropyl)phenyl]propanal, 3-(3-(2-hydroxy-2-methylpropyl)phenyl)propanal or 3-[4-(2-hydroxy-2-methylpropyl)phenyl]butanal.

When the odor of the invention's compounds is compared with that of the prior art compound cited above, then the invention's compounds distinguish themselves by a clearly different odor and by lacking the woody, green, peachy connotation.

Interestingly, the invention's compounds could be seen also as de-hydroxylated analogues of the well-known family including 3-(4-isopropylphenyl)-2-methylpropanal and 3-(4-isobutylphenyl)-2-methylpropanal which possess too lily of the valley note. However, the invention's compounds when compared to these prior art compounds do lack of at least the green, fatty aspect so present in these ingredients profiles. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

In particular, said method or use can be directed to a method the replace Lyral® in perfuming compositions. Or similarly to confer, enhance, improve or modify the floral, lily of the valley, hydroxycitronellal odor note of a perfuming composition or of a perfumed article.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

As solid carrier it is meant a material where the perfuming composition or some element of the perfuming composition can be chemically or physically bound. In general such solid carriers are employed either to stabilize the composition, either to control the rate of evaporation of the compositions or of some ingredients. The employment of solid carrier is of current use in the art and a person skilled in the art knows how to reach the desired effect. However by way of non-limiting example as solid carriers one may cite absorbing gums or polymers or inorganic material, such as porous polymers, cyclodextrines, wood based materials, organic or inorganic gels, clays, gypsum talc or zeolites.

As other non-limiting example of solid carrier one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques are have been described in the prior art), and optionally in the presence of polymeric stabilizer or a cationic copolymer.

In particular, as resins one may cite the ones produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cy Mel® (origin: Cytec Technology Corp.), Urecoll® or Luracoll® (origin: BASF).

In particular, as resins one may cite the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinence, which also address suitable uses of such microcapsules, are represented for example by the article of H. Y. Lee et al. in Journal of Microencapsulation, 2002, vol. 19, pages 559-569, international patent publication WO 01/41915 or yet the article of S. Bône et al. in Chimia, 2011, vol. 65, pages 177-181.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin or even pro-perfumes (i.e. compounds which upon degradation liberate a perfuming ingredient). Examples of pro-perfumes have been described in the literature such as in the article published by A. Herrmann in Angewandte Chemie International Edition, 2007, vol. 46, p. 5836-5863 or in more recent work of similar type, as well as in the abundant patent literature in the field.

In particular one may cite perfuming co-ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: eucalyptus oil, camphor, eucalyptol, menthol and/or alpha-pinene;
  Balsamic ingredients: coumarine, ethylvanillin and/or vanillin;
  Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
  Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethyl-cyclopenta-[G]isochromene, (1S,1'R)-2-[1-(3',3'-dimethyl-1'-cyclohexyl)ethoxy]-2-methylpropyl propanoate, and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

In particular, one may cite the following perfuming co-ingredients, having floral notes: Methyl dihydrojasmonate, linalool, 3-(4-tert-butylphenyl)-2-methylpropanal, hexylcinnamic aldehyde, tetrahydro-2-isobutyl-4-methyl-4(2H)-pyranol, 3,7-dimethyl-1,6-nonadien-3-ol, 3-(4-isopropylphenyl)-2-methylpropanal, 4-cyclohexyl-2-methyl-2-butanol, high cis methyl dihydrojasmonate, tetrahydro linalool.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments), preservative (e.g. antibacterial or antimicrobial or antifungi or anti irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as a perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a splash or eau de parfum, a cologne or an shave or after-shave lotion; a fabric care product, such as a liquid or solid detergent, a fabric softener, a fabric refresher, an ironing water, a paper, or a bleach, carpet cleaners, curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a skin cream or lotion, a vanishing cream or a deodorant or antiperspirant (e.g. a spray or roll on), hair remover, tanning or sun or after sun product, nail products, skin cleansing, a makeup); or a skin-care product (e.g. a perfumed soap, shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, furnisher care, wipe, a dish detergent or hard-surface (e.g. a floor, bath, sanitary or a windows) detergent; a leather care product; a car care product, such as a polish, waxes or a plastic cleaners.

Some of the above-mentioned perfuming consumer product may represent an aggressive medium for the invention's compound, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01%, or even of 1%, to 15%, or even 25%, by weight, or even more, of the compounds of the invention based on the weight of the composition into which they are incorporated. Concentrations lower than these, such as in the order of 0.01% to 1%, or even 2%, by weight, can be used when these compounds are incorporated into perfuming consumer products, percentage being relative to the weight of the article.

The invention's compounds can be prepared according to a method implying the preparation of the corresponding diol and then its oxidation into the desired aldehyde, as reported in the Examples. It is understood that the final product may comprise various isomers, such as the ortho, para or meta products depending on the purity of the staring materials.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

3-[4-(2-hydroxy-2-methylpropyl)phenyl]propanal

Step 1: 3-[4-(2-hydroxy-2-methylpropyl)phenyl]propanol

To a solution of 3-(4-bromophenyl)propan-1-ol (22.8 g, 106 mmol, 1 equiv.) in THF (1.06 L) at −78° C. was added n-BuLi (1.6 M, 358 mL, 573 mmol, 5.4 equiv.) dropwise. After stirring at −78° C. for 5 hours, the temperature was allowed to reach −50° C. and isobutylene oxide (47.1 mL, 530 mmol, 5 equiv.) was added dropwise. After stirring at −50° C. for 30 min, boron trifluoride etherate (101 mL, 796 mmol, 7.5 equiv.) was added dropwise. After stirring at −50° C. for 1 h30, the reaction was quenched with a 10% w/w solution of Na/K tartrates and the mixture was allowed to reach room temperature overnight. It was extracted three times with ether, the combined organic extracts were dried over sodium sulfate and the solvent was evaporated. Lighter impurities were removed by bulb-to-bulb distillation (100-120° C., 10 mbar) to afford 3-[4-(2-hydroxy-2-methylpropyl)phenyl]propanol as an oil (11.5 g, 52% yield) that solidified upon standing.

$^1H$ NMR: 1.22 (s, 6H), 1.44 (s, 2H), 1.85-1.92 (m, 2H), 2.65-2.73 (m, 2H), 2.73 (s, 2H), 3.67 (t, J=6.4, 2H), 7.12-7.14 (m, 4H).

$^{13}C$ NMR: 140.0 (s), 135.2 (s), 130.5 (d, 2C), 128.3 (d, 2C), 70.8 (s), 62.3 (t), 49.3 (t), 34.2 (t), 31.7 (t), 29.2 (q, 2C).

Step 2: 3-[4-(2-hydroxy-2-methylpropyl)phenyl]propanal

To a suspension of the alcohol of step 1 (11.9 g, 57.1 mmol, 1 equiv.) in $CH_2Cl_2$ (380 mL) at room temperature was added finely grinded PCC (24.6 g, 114 mmol, 2 equiv.) portionwise. The reaction was stirred at room temperature for 45 min before being filtered on a celite pad using ether as an eluant. The solvent was evaporated and the residue was purified by flash column chromatography on silica gel (Heptane/AcOEt 75:25) and bulb-to-bulb distillation (135° C., 0.16-0.19 mbar) to afford the desired aldehyde as an oil (4.99 g, 42% yield).

$^1H$ NMR: 1.21 (s, 6H), 2.73 (s, 2H), 2.75-2.79 (m, 2H), 2.94 (t, J=7.4, 2H), 7.13 (s, 4H), 9.81 (t, J=1.4, 1H).

$^{13}C$ NMR: 201.6 (s), 138.4 (s), 135.8 (s), 130.7 (d, 2C), 128.1 (d, 2C), 70.7 (s), 49.3 (t), 45.2 (t), 29.2 (q, 2C), 27.7 (t).

3-(3-(2-hydroxy-2-methylpropyl)phenyl)propanal

Step 1: 3-[3-(2-hydroxy-2-methylpropyl)phenyl]propanol

To a solution of 3-(3-bromophenyl)propan-1-ol (5.0 g, 23 mmol, 1 equiv.) in THF (230 mL) at −78° C. was added n-BuLi (1.6 M, 78 mL, 126 mmol, 5.4 equiv.) dropwise. After stirring at −78° C. for 5 hours, the temperature was allowed to reach −50° C. and isobutylene oxide (10.3 mL, 116 mmol, 5 equiv.) was added dropwise. After stirring at −50° C. for 30 min, boron trifluoride etherate (22.1 mL, 174 mmol, 7.5 equiv.) was added dropwise. After stirring at −50° C. for 1 h30, the reaction was quenched with a 10% w/w solution of Na/K tartrates and the mixture was allowed to reach room temperature overnight. It was extracted three times with ether, the combined organic extracts were dried over sodium sulfate and the solvent was evaporated. Lighter impurities were removed by bulb-to-bulb distillation (100-120° C., 10 mbar) to afford crude 3-[3-(2-hydroxy-2-methylpropyl)phenyl]propanol that was used as such for the next step.

Step 2: 3-[3-(2-hydroxy-2-methylpropyl)phenyl]propanal

To a suspension of the crude alcohol of step 1 (4.84 g, 23 mmol, 1 equiv.) in $CH_2Cl_2$ (155 mL) at room temperature was added finely grinded PCC (10.0 g, 46 mmol, 2 equiv.) portionwise. The reaction was stirred at room temperature for 45 min before being filtered on a celite pad using ether as an eluant. The solvent was evaporated and the residue was purified by flash column chromatography on silica gel (Heptane/AcOEt 75:25) and bulb-to-bulb distillation (135° C., 0.16-0.19 mbar) to afford the desired aldehyde as an oil (929 mg, 19% yield on 2 steps).
$^1$H NMR: 1.22 (s, 6H), 2.74 (s, 2H), 2.78 (dt, J=7.5, 1.3, 2H), 2.95 (t, J=7.5, 2H), 7.05-7.09 (m, 3H), 7.22-7.26 (m, 1H), 9.81 (t, J=1.3, 1H).
$^{13}$C NMR: 201.6 (s), 140.2 (s), 138.1 (s), 130.5 (d), 128.5 (d), 128.4 (d), 126.4 (d), 70.7 (s), 49.6 (t), 45.2 (t), 29.2 (q, 2C), 28.1 (t).

3-[4-(2-hydroxy-2-methylpropyl)-2-methylphenyl]propanal

Step 1: Methyl (E)-3-(4-bromo-2-methylphenyl)acrylate

To a mixture of 4-bromo-2-methylbenzaldehyde (5.87 mL, 44 mmol, 1 equiv.) and trimethyl phosphonoacetate (7.62 mL, 53 mL, 1.2 equiv.) was added potassium carbonate (12.1 g, 88 mmol, 2 equiv.) and DBU (0.2 mL, 1.3 mmol, 0.03 equiv.). The reaction was stirred at room temperature for 19 h before being quenched with water. It was extracted three times with ether, the combined organic extracts were dried over sodium sulfate and the solvent was evaporated. The residue was purified by bulb-to-bulb distillation (135-140° C., 0.15 mbar) to afford methyl (E)-3-(4-bromo-2-methylphenyl)acrylate (10.3 g, 92% yield).
$^1$H NMR: 2.40 (s, 3H), 3.81 (s, 3H), 6.34 (d, J=15.9, 1H), 7.32.7.40 (m, 3H), 7.87 (d, J=15.9, 1H).
$^{13}$C NMR: 167.2 (s), 141.3 (d), 139.6 (s), 133.6 (d), 132.4 (s), 129.6 (d), 127.8 (d), 124.1 (s), 119.5 (d), 51.8 (q), 19.6 (q).

Step 2: Methyl 3-(4-bromo-2-methylphenyl)propanoate

In a 120-mL autoclave were introduced methyl (E)-3-(4-bromo-2-methylphenyl)acrylate (12.0 g, 47 mmol) and 5% Pd/C (102 mg) in ethyl acetate (50 mL). The autoclave was sealed, purged with nitrogen and reacted at room temperature under 18 bar pressure of $H_2$. After one hour, the autoclave was purged with nitrogen, opened, the catalyst was filtered and the solvent was evaporated. The residue was purified by bulb-to-bulb distillation (130° C., 6-7 mbar) to afford methyl 3-(4-bromo-2-methylphenyl)propanoate (8.12 g, 81% purity, 55% yield).
$^1$H NMR: 2.29 (s, 3H), 2.56 (t, J=7.9, 2H), 2.89 (t, J=7.9, 2H), 3.68 (s, 3H), 6.99-7.30 (m, 3H).

$^{13}$C NMR: 173.1 (s), 138.3 (s), 137.6 (s), 133.0 (d), 130.2 (d), 129.1 (d), 120.0 (s), 51.7 (q), 34.2 (t), 27.8 (t), 19.1 (q).

Step 3: 3-(4-bromo-2-methylphenyl)propan-1-ol

To a suspension of lithium aluminum hydride (8.08 g, 31 mmol, 1 equiv.) in THF (31 mL) at 0° C. was added a solution of methyl 3-(4-bromo-2-methylphenyl)propanoate (8.08 g, 31 mmol, 1 equiv.) in THF (31 mL) dropwise. After stirring for 2 h at r.t., the reaction was cooled down to 0° C. and quenched successively with 3.5 mL of water, 10.5 mL of a 5% NaOH solution and 3.5 mL of water. It was extracted three times with ether, the combined organic extracts were dried over sodium sulfate and the solvent was evaporated. The crude product was used as such for the next step.

Step 4: 3-(4-(2-hydroxy-2-methylpropyl)-2-methylphenyl)propan-1-ol

To a solution of crude 3-(4-bromo-2-methylphenyl)propan-1-ol (6.99 g, 22 mmol, 1 equiv.) in THF (220 mL) at −78° C. was added n-BuLi (1.6 M, 74.2 mL, 119 mmol, 5.4 equiv.) dropwise. After stirring at −78° C. for 5 hours, the temperature was allowed to reach −50° C. and isobutylene oxide (9.76 mL, 110 mmol, 5 equiv.) was added dropwise. After stirring at −50° C. for 30 min, boron trifluoride etherate (20.9 mL, 165 mmol, 7.5 equiv.) was added dropwise. After stirring at −50° C. for 1 h30, the reaction was quenched with a 10% w/w solution of Na/K tartrates and the mixture was allowed to reach room temperature overnight. It was extracted three times with ether, the combined organic extracts were dried over sodium sulfate and the solvent was evaporated. Lighter impurities were removed by bulb-to-bulb distillation (100-120° C., 10 mbar) to afford crude 3-(4-(2-hydroxy-2-methylpropyl)-2-methylphenyl)propan-1-ol that was used as such for the next step.

Step 5: 3-(4-(2-hydroxy-2-methylpropyl)-2-methylphenyl)propanal

To a suspension of the crude 3-(4-(2-hydroxy-2-methylpropyl)-2-methylphenyl)propan-1-ol (4.89 g, 22 mmol, 1 equiv.) in $CH_2Cl_2$ (147 mL) at room temperature was added finely grinded PCC (5.69 g, 26 mmol, 1.2 equiv.) portionwise. The reaction was stirred at room temperature for 45 min before being filtered on a celite pad using ether as an eluant. The solvent was evaporated and the residue was purified by flash column chromatography on silica gel (Heptane/AcOEt 75:25) and bulb-to-bulb distillation (135° C., 0.16-0.19 mbar) to afford the desired aldehyde as an oil (910 mg, 19% yield on 3 steps).
$^1$H NMR: 1.22 (s, 6H), 2.30 (s, 3H), 2.70 (s, 2H), 2.73 (dt, J=7.7, 1.4 Hz, 2H), 2.92 (t, J=7.7 Hz, 2H), 6.97-7.00 (m, 2H), 7.06 (d, J=7.6 Hz, 1H), 9.84 (t, J=1.4 Hz, 1H).
$^{13}$C NMR: 201.6 (s), 136.6 (s), 135.9 (s), 135.7 (s), 132.5 (d), 128.4 (d), 128.3 (d), 70.7 (s), 49.2 (t), 44.0 (t), 29.2 (q, 2C), 25.1 (t), 19.3 (q).

3-[4-(3-hydroxy-3-methylbutyl)phenyl]propanal

Step 1: Methyl-3-(4-(3-hydroxy-3-methylbut-1-yn-1-yl)phenyl)acrylate

To a solution of 4-(3-hydroxy-3-methylbut-1-yn-1-yl) benzaldehyde (5.02 g, 27 mmol, 1 equiv.) and trimethyl phosphonoacetate (4.24 mL, 29 mmol, 1.1 equiv.) in cyclohexane (50 mL) at 50° C. was added sodium methanolate (5.4 M in methanol, 5.93 mL, 32 mmol, 1.2 equiv.). After stirring for 2 h, the reaction was quenched with a saturated solution of ammonium chloride. It was extracted three times with ether, the combined organic extracts were dried over sodium sulfate and the solvent was evaporated. The crude product was used as such for the next step.

Step 2: Methyl 3-(4-(3-hydroxy-3-methylbutyl)phenyl)propanoate

To a solution of crude ester from step 1 (6.52 g, 24 mmol, 1 equiv.) in ethyl acetate (60 mL) was added 5% Pd/C (187 mg) and the suspension was stirred under a 1 bar hydrogen atmosphere for 15 h. The catalyst was filtered, the solvent was evaporated and the product was purified by bulb-to-bulb distillation (145-150° C., 0.15 mbar) to afford methyl 3-(4-(3-hydroxy-3-methylbutyl)phenyl)propanoate (4.11 g, 68% yield on 2 steps) as an oil.

$^1$H NMR: 1.28 (s, 6H), 1.76-1.79 (m, 2H), 2.62 (t, J=7.9, 2H), 2.66-2.68 (m, 2H), 2.92 (t, J=7.9, 2H), 3.67 (s, 3H), 7.10-7.14 (m, 4H).

$^{13}$C NMR: 173.4 (s), 140.5 (s), 137.9 (s), 128.5 (d, 2C), 128.3 (d, 2C), 70.9 (s), 51.6 (q), 45.7 (t), 35.8 (t), 30.5 (t), 30.3 (t), 29.3 (q, 2C).

Step 3: 3-(4-(3-hydroxy-3-methylbutyl)phenyl)propanal

To a solution of ester from step 2 (4.11 g, 16.4 mmol, 1 equiv.) in dichloromethane (41 mL) at −78° C. was added DIBAL (1 M in hexanes, 41 mL, 41 mmol, 2.5 equiv.) over a 3 hours period. After stirring for 1 h 30, the reaction was quenched with a 10% w/w solution of Na/K tartrates and the mixture was allowed to reach room temperature overnight. It was extracted three times with ether, the combined organic extracts were dried over sodium sulfate and the solvent was evaporated. The residue was purified by flash column chromatography on silica gel (Heptane/AcOEt 6:4 to 4:6) and bulb-to-bulb distillation (145-150° C., 0.068-0.073 mbar) to afford 3-(4-(3-hydroxy-3-methylbutyl)phenyl)propanal (2.08 g, 58% yield) as an oil.

$^1$H NMR: 1.28 (s, 6H), 1.75-1.78 (m, 2H), 2.66-2.68 (m, 2H), 2.76 (dt, J=7.6, 1.3, 2H), 2.92 (t, J=7.6, 2H), 7.10-7.14 (m, 4H), 9.81 (t, J=1.3, 1H).

$^{13}$C NMR: 201.8 (s), 140.5 (s), 137.6 (s), 128.5 (d, 2C), 128.3 (d, 2C), 70.9 (s), 45.7 (t), 45.3 (t), 30.3 (t), 29.3 (q, 2C), 27.7 (t).

Example 2

Preparation of a Perfuming Composition

A woman's perfume, of the musky type, was prepared by admixing the following ingredients:

| Parts by weight | Ingredient |
|---|---|
| 40 | Hexyl acetate |
| 80 | Benzyl acetate |
| 20 | Cinnamyl acetate |
| 80 | 1%* 4-Methylphenyl acetate |
| 20 | Alcool Cinnamique |
| 10 | Anethol |
| 20 | 10%* 7-isopropyl-2h,4h-1,5-benzodioxepin-3-one |
| 50 | Coranol ® [1] |
| 20 | Coumarine |
| 40 | 10%* Tarragon oil |
| 10 | 2-Methyl-4-(2,2,3-trimethyl-3-cyclopenten-1-yl)-4-penten-1-ol [a] |
| 170 | Florol ® [2] |
| 3100 | 70%** Galaxolide |
| 60 | 1%* Gamma Nonalactone |
| 40 | Clove essential oil |
| 1800 | Hedione ® HC [3] |
| 500 | Helvetolide ® [4] |
| 40 | Hivernal ® [5] |
| 50 | Iralia ® Total [6] |
| 300 | (2E)-2-methyl-3-(4-methylphenyl)-2-propen-1-ol [a] |
| 400 | Lilial ® [7] |
| 400 | Linalool |
| 40 | Methylisoeugenol |
| 20 | 10%* Methylnaphtylcetone |
| 600 | Muscenone ® [8] Delta |
| 100 | Muscone Laevo |
| 50 | Amyl salicylate |
| 50 | Sclareolate ® [9] |
| 40 | Vanilline |
| 400 | Wardia ® [10] |
| 50 | (1S,2S,3S)-2,6,6-trimethyl-bicyclo[3.1.1]heptane-3-spiro-2'-cyclohexen-4'-one |
| 100 | Ylang Extra |
| 8700 | |

*in dipropyleneglycol
**in isopropyle myristate
[1] 4-cyclohexyl-2-methyl-2-butanol [a]
[2] tetrahydro-2-isobutyl-4-methyl-4(2H)-pyranol [a]
[3] cis methyl dihydrojasmonate [a]
[4] (1S,1'R)-2-[1-(3',3'-dimethyl-1'-cyclohexyl)ethoxy]-2-methylpropyl propanoate [a]
[5] 3-(3,3/1,1-dimethyl-5-indanyl)propanal [a]
[6] mixture of methylionones isomers [a]
[7] 3-(4-tert-butylphenyl)-2-methylpropanal [a]
[8] 3-methyl-5-cyclopentadecen-1-one [a]
[9] propyl (S)-2-(1,1-dimethylpropoxy)propanoate [a]
[10] compounded floral perfumery base [a]
[a] origin: Firmenich SA, Geneva, Switzerland The addition of 1300 parts by weight of 3-[4-(2-hydroxy-2-methylpropyl)phenyl]propanal to the above-described fragrance imparted to the latter an amazing warmness, and floral volume associated with a "wetty" effect that only Lyral® could be able to impart. The invention's compound proved to be an excellent substitute for this palette ingredient.

Example 3

Preparation of a Perfuming Composition

A perfuming composition, of the chypre type, was prepared by admixing the following ingredients:

| Parts by weight | Ingredient |
|---|---|
| 300 | Benzyl acetate |
| 50 | Geranyl acetate |
| 150 | 1%* 4-Methylphenyl acetate |
| 10 | 10%* Phenylacetic acide |
| 40 | Cinnamic alcohol |
| 90 | 10%* 10-Undecenal |
| 60 | 1-(2,6,6-Trimethyl-2-cyclohexen-1-yl)-1,6-heptadien-3-one |
| 350 | Animalis [c] |
| 20 | Artemisia oil |
| 500 | Bergamot oil |
| 80 | (−)-(8R)-8,12-epoxy-9βH-13,14,15,16-tetranorlabdane [a] |
| 80 | 8-Methoxy-2,6,6,8-tetramethyl-tricyclo[5.3.1.0(1,5)]undecane |
| 20 | Cis-3-hexenol |
| 250 | Citronellol |
| 600 | Clearwood ® [1] |
| 100 | Coumarine |

-continued

| Parts by weight | Ingredient |
|---|---|
| 50 | Cyclosal ® [2)] |
| 50 | 10%* Damascone Alpha |
| 50 | 10%* Tarragon |
| 150 | Eugenol |
| 300 | Exaltolide ® [3)] Total |
| 60 | 10%* Violet leaves oil |
| 150 | 3-(4-Methoxyphenyl)-2-methylpropanal |
| 20 | Galbanum Essential oil |
| 60 | Gamma Decalactone |
| 50 | Gamma Undecalactone |
| 100 | Geraniol |
| 350 | Hedione ® [4)] HC |
| 20 | Heliotropine |
| 100 | Hydroxycitronellal |
| 20 | Indol |
| 700 | Iso E ® Super [5)] |
| 250 | Linalool |
| 150 | Mandarin oil |
| 500 | Alpha Iso Methylionone |
| 20 | 10%* 2-Methylundecanal |
| 80 | Mousse Chene |
| 100 | Crystal moss |
| 500 | Muscenone ® Delta [6)] |
| 80 | Myrrhone ® [7)] |
| 500 | Patchouli oil |
| 120 | Phenethylol |
| 120 | Pepper oil |
| 500 | Benzyl 2-hydroxybenzoate |
| 250 | Cis-3-hexenol salicylate |
| 20 | Terpineol Alpha |
| 60 | 10%* Vanilline |
| 640 | (1S,2S,3S)-2,6,6-trimethyl-bicyclo[3.1.1]heptane-3-spiro-2'-cyclohexen-4'-one |
| 180 | Ylang |
| 9000 | |

*in dipropyleneglycol
[1)] terpene fraction corresping to patchouili oil [a)]
[2)] 3-(4-isopropylphenyl)-2-methylpropanal [b)]
[3)] pentadecanolide [a)]
[4)] methyl cis-dihydrojasmonate [a)]
[5)] 1-(octahydro-2,3,8,8-tetramethyl-2-naphthalenyl)-1-ethanone [b)]
[6)] 3-methyl-5-cyclopentadecen-1-one [a)]
[7)] 4-(2,2,C-3,T-6-tetramethyl-R-1-cyclohexyl)-3-buten-2-one [a)]
[c)] compounded perfumery base [a)]
[a)] origin: Firmenich SA, Geneva, Switzerland
[b)] origin: International Flavors & Fragrances, USA The addition of 1000 parts by weight of 3-[4-(2-hydroxy-2-methylpropyl)phenyl]propanal to the above-described composition imparted to the latter a remarkable radiance, and volume associated with a floral, wetty twist very close to the one obtained when instead of the invention's compound it was added Lyral®.

The invention claimed is:

1. A compound of formula

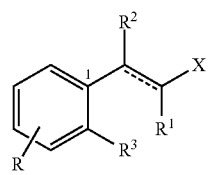

(I)

in the form of any one of its stereoisomers or a mixture thereof, and wherein
the dotted line represents a carbon-carbon single or double bond;
X represents a CN or CHO group;
$R^1$ represents a hydrogen atom and each $R^2$ and $R^3$ independently from each other represents a hydrogen atom or a $C_{1-2}$ alkyl group; and
R represents a group of formula $[CH_2]_nC(Me)_2OH$, wherein n is 1 or 2; said R being a meta or para substituent of the aromatic ring, relative position 1;
wherein the compound of formula (I) imparts odor notes of the lily of the valley.

2. A compound according to claim 1, wherein the compound comprises formula

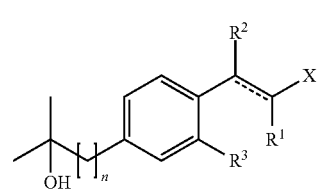

(II)

in the form of any one of its stereoisomers or a mixture thereof, and wherein
the dotted line represents a carbon-carbon single or double bond;
n is 1 or 2;
X represents a CN or CHO group; and
$le$ represents a hydrogen atom and each $R^2$ and $R^3$ independently from each other represents a hydrogen atom or a $C_{1-2}$ alkyl group.

3. A compound according to claim 1, wherein the compound comprises formula

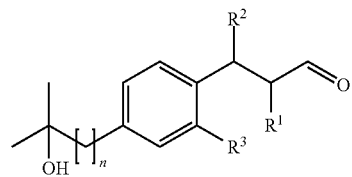

(IV)

wherein n, $R^2$ and $R^3$ are as defined in claim 1.

4. A compound according to claim 1, characterized in that n is 1.

5. A compound according to claim 1, characterized in that one of $R^2$ and $R^3$ is a hydrogen atom, and the other a methyl group.

6. A compound according to claim 1, wherein the compound is 3-[4-(2-hydroxy-2-methylpropyl)phenyl]propanal.

7. A perfuming composition comprising
i) at least one compound of formula (I) of claim 1;
ii) at least one ingredient selected from the group consisting of a perfumery carrier and a perfumery base; and
iii) optionally at least one perfumery adjuvant.

8. A perfuming consumer product comprising at least one compound of formula (I) of claim 1.

9. A perfuming consumer product according to claim 8, characterized in that the perfumery consumer product is a perfume, a fabric care product, a body-care product, a cosmetic preparation, a skin-care product, an air care product or a home care product.

10. A perfuming consumer product according to claim 8, characterized in that the perfumery consumer product is a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, a car care product.

11. A method to confer, enhance, improve or modify the odor properties of a perfuming composition or of a perfumed article, which method comprises adding to said composition or article an effective amount of at least one compound of formula (I) of claim 1.

12. A compound of formula

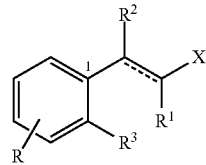

(I)

in the form of any one of its stereoisomers or a mixture thereof, and wherein the dotted line represents a carbon-carbon single or double bond;

X represents a CN or CHO group;

each $R^1$, $R^2$ and $R^3$ independently from each other, represents a hydrogen atom or a $C_{1-2}$ alkyl group; and R represents a group of formula $[CH_2]_nC(Me)_2OH$, wherein n is 1 or 2; said R being a para substituent of the aromatic ring, relative to position 1, wherein the compound is a perfuming ingredient; and wherein the compound of formula (I) imparts odor notes of the lily of the valley.

13. A compound according to claim 12, wherein the compound comprises formula

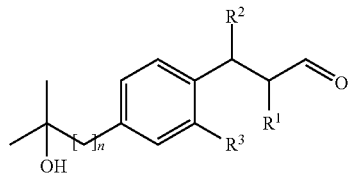

(IV)

wherein n, $R^1$, $R^2$ and $R^3$ are as defined in claim 12.

14. A compound according to claim 12, characterized in that n is 1.

* * * * *